(12) United States Patent
Kalloo et al.

(10) Patent No.: US 11,317,900 B2
(45) Date of Patent: May 3, 2022

(54) METHOD AND DEVICE FOR TISSUE ACQUISITION OR CLOSURE

(71) Applicant: THE JOHNS HOPKINS UNIVERSITY, Baltimore, MD (US)

(72) Inventors: Anthony N. Kalloo, Baltimore, MD (US); Mouen A. Khashab, Towson, MD (US); Robert R. Ragland, Temecula, CA (US); Darrin J. Kent, Murrieta, CA (US); Eric T. Johnson, Temecula, CA (US)

(73) Assignee: The Johns Hopkins University, Baltimore, MD (US)

( * ) Notice: Subject to any disclaimer, the term of this patent is extended or adjusted under 35 U.S.C. 154(b) by 291 days.

(21) Appl. No.: 15/747,214

(22) PCT Filed: Jul. 22, 2016

(86) PCT No.: PCT/US2016/043614
§ 371 (c)(1),
(2) Date: Jan. 24, 2018

(87) PCT Pub. No.: WO2017/019525
PCT Pub. Date: Feb. 2, 2017

(65) Prior Publication Data
US 2018/0242960 A1 Aug. 30, 2018

Related U.S. Application Data

(60) Provisional application No. 62/196,741, filed on Jul. 24, 2015.

(51) Int. Cl.
*A61B 17/00* (2006.01)
*A61B 17/12* (2006.01)
*A61B 17/50* (2006.01)

(52) U.S. Cl.
CPC .... *A61B 17/0057* (2013.01); *A61B 17/12013* (2013.01); *A61B 17/50* (2013.01); *A61B 2017/0061* (2013.01); *A61B 2017/0065* (2013.01); *A61B 2017/00243* (2013.01); *A61B 2017/00269* (2013.01); *A61B 2017/00349* (2013.01); *A61B 2017/00575* (2013.01);
(Continued)

(58) Field of Classification Search
CPC .......... A61B 17/0057; A61B 17/12009; A61B 17/12013; A61B 17/50; A61B 2017/00349; A61B 2017/00358; A61B 2017/00575; A61B 2017/00579; A61B 2017/00584; A61B 2017/00588; A61B 2017/00592; A61B 2017/00597; A61B 2017/0061; A61B 2017/00615; A61B 2017/00623; A61B 2017/00632; A61B 2017/00637; A61B 2017/00641
See application file for complete search history.

(56) References Cited

U.S. PATENT DOCUMENTS

| | | | | |
|---|---|---|---|---|
| 5,120,308 A | * | 6/1992 | Hess | A61M 25/09 600/434 |
| 2002/0147456 A1 | * | 10/2002 | Diduch | A61B 17/0469 606/144 |

(Continued)

*Primary Examiner* — Robert A Lynch
(74) *Attorney, Agent, or Firm* — Johns Hopkins Technology Ventures

(57) ABSTRACT

The present disclosure provides a device and methods for acquiring tissue within a lumen or for closure of bodily openings.

38 Claims, 18 Drawing Sheets

(52) U.S. Cl.
CPC ............... *A61B 2017/00584* (2013.01); *A61B 2017/00592* (2013.01); *A61B 2017/00659* (2013.01); *A61B 2017/00668* (2013.01); *A61B 2017/00818* (2013.01); *A61B 2017/00876* (2013.01)

(56) References Cited

U.S. PATENT DOCUMENTS

| | | |
|---|---|---|
| 2007/0083232 A1 | 4/2007 | Lee |
| 2007/0198058 A1 | 8/2007 | Gelbart et al. |
| 2009/0254119 A1 | 10/2009 | Sibbitt et al. |
| 2010/0152732 A1* | 6/2010 | Katou ................ A61B 18/1492 606/49 |
| 2010/0286719 A1* | 11/2010 | Paul .................. A61B 17/3207 606/159 |
| 2011/0125091 A1* | 5/2011 | Abbate ................... A61F 2/186 604/96.01 |
| 2013/0041405 A1 | 2/2013 | Gelbart |
| 2013/0225900 A1 | 8/2013 | Kalloo et al. |
| 2015/0018848 A1* | 1/2015 | Kappel ................ A61B 17/122 606/140 |

\* cited by examiner

METHOD AND DEVICE FOR TISSUE ACQUISITION OR CLOSURE

CROSS-REFERENCE TO RELATED APPLICATIONS

This application is a 35 U.S.C. § 371 U.S. national entry of International Application PCT/US2016/043614 having an international filing date of Jul. 22, 2016, which claims the benefit of U.S. Provisional Application No. 62/196,741, filed Jul. 24, 2015, the content of each of the aforementioned applications is herein incorporated by reference in their entirety.

BACKGROUND OF THE INVENTION

Field of the Invention

The invention relates generally to surgical devices and methods and more specifically to a device and methods for acquiring tissue or closing an opening in bodily tissue.

Background Information

Perforations in tissue or bodily walls may be formed intentionally or unintentionally. For example, an unintentional ventral abdominal hernia may be formed in the abdominal wall due to heavy lifting, coughing, strain imposed during a bowel movement or urination, fluid in the abdominal cavity, or other reasons.

Iatrogenic perforation is a major complication, which is difficult to endoscopically manage, and, if large, inevitably requires surgical repair. Perforations or leaks in the walls of internal organs and vessels may occur naturally (e.g., through rupture of herniated tissue) or formed unintentionally (e.g., as a result of a surgical procedure, such as tissue resection). In the latter respect, increasing practice of endoscopic therapies can increase the incidence of iatrogenic perforation in luminal tissues such as the gastrointestinal (GI) tract. When a perforation is formed in the stomach or intestines, spillage of the stomach contents, intestinal contents or other bodily fluids into the adjacent body cavity can occur, providing a potentially deadly environment for infection.

To minimize leakage of bowel contents, risk for severe peritonitis, and abscess formation, prompt repair of the perforation site is highly desirable. An urgent surgical closure remains the primary standard treatment for acute perforation. Devices for use in closing perforations and leaks generally involve deployment of clips, sutures, adhesives, patches or tissue anchors to join adjacent tissues together around the opening. The closure device is often introduced to the surgical site endoscopically or laparoscopically, and used in conjunction with tissue graspers or other devices to orient the tissue for closure. However, the efficacy of such devices has been suboptimal.

Intentional perforations may be formed, for example, during surgical procedures such as translumenal procedures. In a translumenal procedure, one or more instruments, such as an endoscope, may be inserted through a visceral wall, such as the stomach wall. During a translumenal procedure, a closure instrument may be used to close the perforation in the visceral wall. Depending on the structure comprising the perforation, it may be difficult to adequately close the perforation and prevent leakage of bodily fluids.

A need therefore remains for a device which can be used for treatment of intraluminal leaks and perforations, including for example, gastrointestinal perforations, fistulas and anastomotic leaks, along with other bodily openings, such as hernias as well as cardiac, esophageal, gastric, intestinal and colonic perforations and defects. In addition, a need exists for improved devices which can be used to acquire tissue or other objects within a bodily lumen.

SUMMARY OF THE INVENTION

In one aspect, the invention provides a device for facilitating closure of a bodily opening or acquiring tissue. The device includes a tissue capturing structure defined by a plurality of arms elongated along a central axis, each arm terminating at a distal tip having a tissue anchoring structure, such as a barb, hook or the like. A central apparatus is disposed along the central axis securing the plurality of arms. The plurality of arms expand radially from the central axis during transition from a compressed (undeployed) state to an expanded (deployed) state thereby forming an expanded tissue capturing structure.

The arms of the device are formed of a biocompatible flexible resilient material, preferably a shape-memory material. The material allows the device to assume a compressed configuration with the arms folded down along the central axis and an expanded configuration with the arms extending radially from the central axis. Placing the device into the first configuration allows the device to be compressed into a delivery tool, such as a delivery catheter or scope device. The device is operable to centralize and align the plurality of arms along the central axis when the device is in the compressed state such that the device has a reduced diameter to facilitate entry into a bodily opening or lumen. Deployment of the device out of the proximal end of the tool allows the device to resiliently assume an expanded configuration as the arms move outwardly from the central axis to define a tissue capturing structure.

In another aspect, the invention provides a system which includes the device of the disclosure in combination with a catheter or scope device and optionally a closure device operable to close a bodily opening.

In still another aspect, the invention provides a method for closure of a bodily opening using the device or system of the disclosure.

In yet another aspect, the invention provides a method for acquiring or resecting tissue at a target site using the device or system of the disclosure.

In another aspect, the invention provides a method for removing a foreign body from a target site in or on a body of a subject using the device or system of the disclosure.

DETAILED DESCRIPTION OF THE INVENTION

Figure 1A:
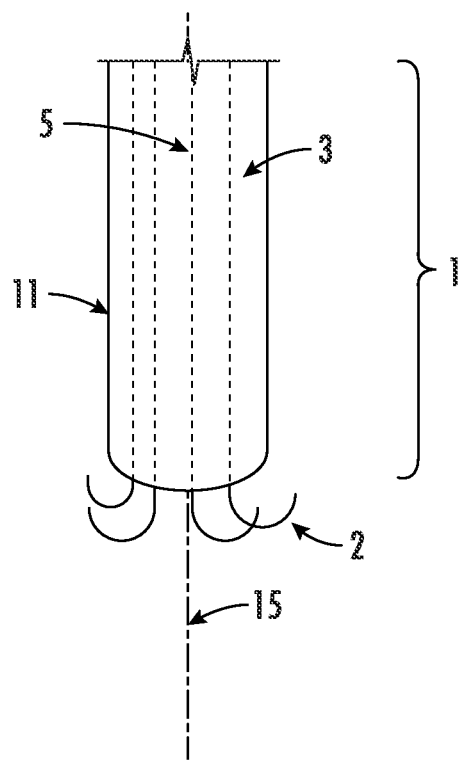
FIG. 1A is a schematic view of a device in one embodiment of the invention in a compressed state.

Before the present compositions and methods are described, it is to be understood that this invention is not limited to particular devices, methods, and experimental conditions described, as such devices, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term scope device or endoscope, as used herein, should be construed as including all types of invasive instruments, flexible, articulating or rigid, having scope features. These include, but are not limited to, colonoscopes, gastroscopes, laparoscopes, and rectoscopes. Similarly, the use of "endoscopic" is to be construed as referring to all types of invasive surgical scopes.

A system, and a device according to this invention will be of particular use in acquisition of objects or tissue in a luminal cavity or an organ surface and facilitate closure of a bodily opening or acquisition and resection of tissue or removal of the foreign object. Without intending to be limiting, the device may be used on any tissue or organ of the body, such as tissue of the circulatory and cardiovascular systems, such as cardiac tissue and vasculature, the digestive system, such as bowel, rectum, gastrointestinal tract, gallbladder, liver, pancreas, stomach, esophagus, pharynx and intestinal tissue, the respiratory system, such as larynx, trachea, lung and diaphragm tissue, the urinary tract, such as kidney, ureter, bladder and urethra tissue, and the reproductive system, such as uterus, ovarian, fallopian, and prostate tissue.

In embodiments, any catheter or scope device having one or more accessory channels may be used to deliver the device of the invention. For example, an endoscope with accessory channels such as the CF2T-160L from Olympus, or DUETTE® from Cook Medical may be used to deliver a closure device of the invention.

In one aspect, the invention provides a device for facilitating closure of a bodily opening or acquiring tissue. The device includes a tissue capturing structure defined by a plurality of arms elongated along a central axis, each arm terminating at a distal tip having a tissue anchoring structure, such as a barb, hook or the like. A central apparatus is disposed along the central axis securing the plurality of arms. The plurality of arms expand radially from the central axis during transition from a compressed (undeployed) state to an expanded (deployed) state thereby forming an expanded tissue capturing structure.

The arms of the device are formed of a biocompatible flexible resilient material, preferably a shape-memory material. The material allows the device to assume a compressed configuration with the arms folded down along the central axis and an expanded configuration with the arms extending radially from the central axis. Placing the device into the first configuration allows the device to be compressed into a delivery tool, such as a delivery catheter or scope device. The device is operable to centralize and align the plurality of arms along the central axis when the device is in the compressed state such that the device has a reduced diameter to facilitate entry into a bodily opening or lumen. Deployment of the device out of the proximal end of the tool allows the device to resiliently assume an expanded configuration as the arms move outwardly from the central axis to define a tissue capturing structure.

Figure 4A:
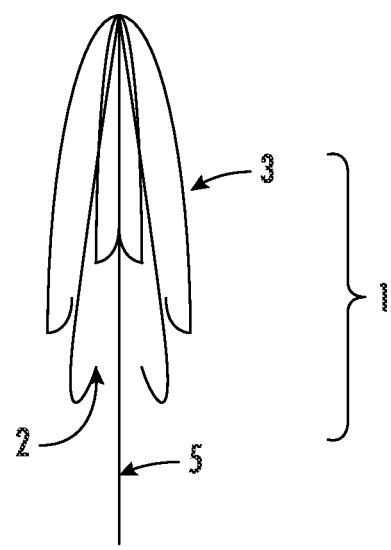
FIG. 4A is a schematic view of a device in one embodiment of the invention in a compressed configuration.

Turning to FIGS. 1 and 4, a device 1 of the invention is shown in its compressed configuration preloaded in catheter 11. Arms 3 are attached at their proximal end to a central apparatus 5, which consists of a push/pull rod, and have hooks 2 at their distal ends. Hooks 2 are oriented such that they face radially outward from the elongated central axis 15 of the device as shown in FIG. 1, or alternatively, hooks 2 are oriented such that they face radially inward toward the elongated central axis 15 of the device as shown in FIG. 4. Arms 3 are moveable from a compressed configuration to an expanded one (see FIGS. 2 and 5). Upon deployment, the arms of the device form a tissue capturing structure which, in embodiments, is essentially an expanded umbrella (FIG. 2) or everted umbrella (FIG. 5) shape, the umbrella being compressed inside a loaded catheter in the undeployed state. The loaded catheter can be introduced through the accessory channel of a scope device and advanced through or adjacent to the perforation under endoscopic visualization. The arms are advanced out of the catheter and expanded to a desired state of expansion to define a tissue capturing structure having a desired diameter depending on the size of the perforation in the case of the closure device, or a targeted lesion (e.g. precancerous mucosa or bleeding ulcer) in the case of the acquisition device.

Figure 1B:
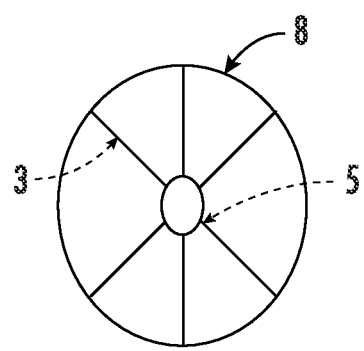
FIG. 1B is a cross-sectional view of the device of FIG. 1A.
Figure 2:
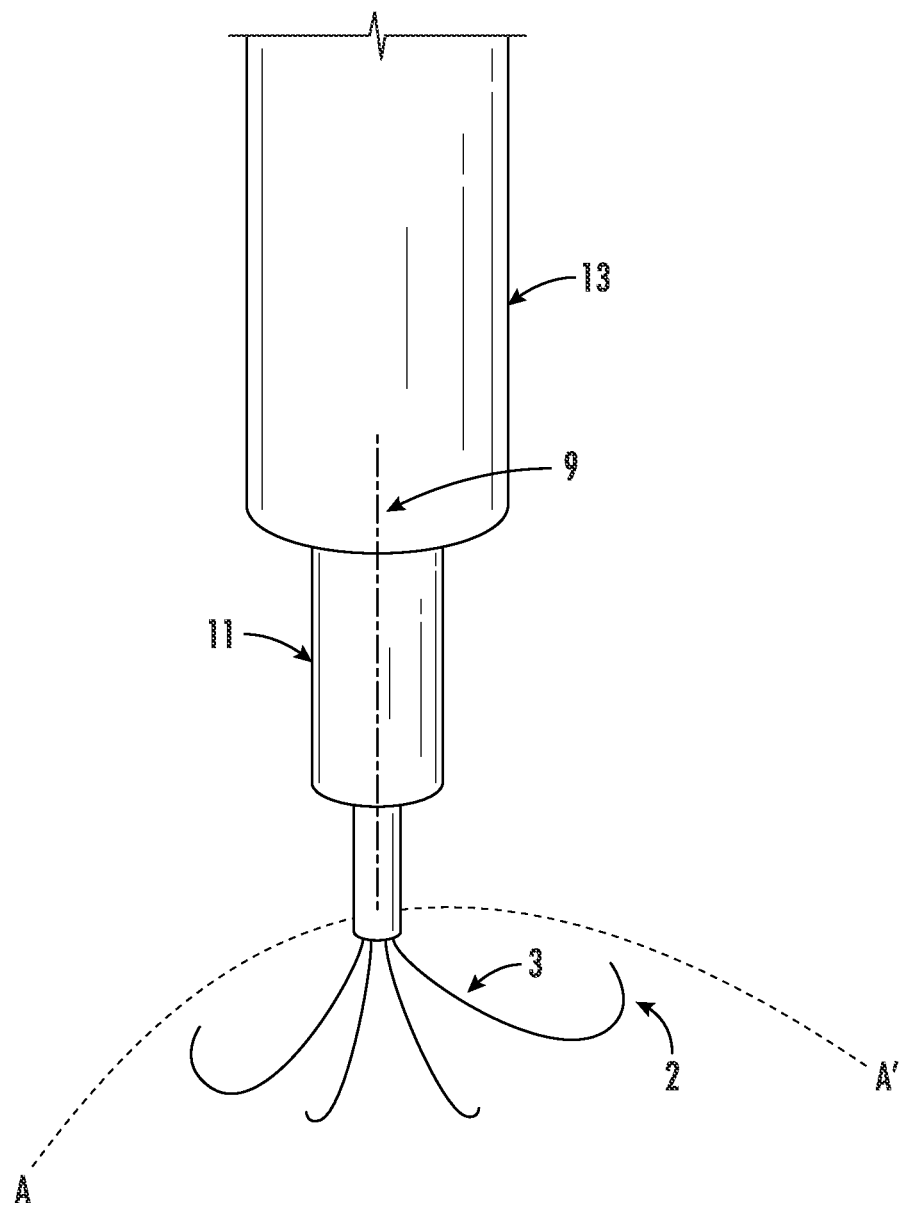
FIG. 2 is a schematic view of a device in one embodiment of the invention being deployed from the proximal end of a loader catheter provided through an endoscope.
Figure 4B:
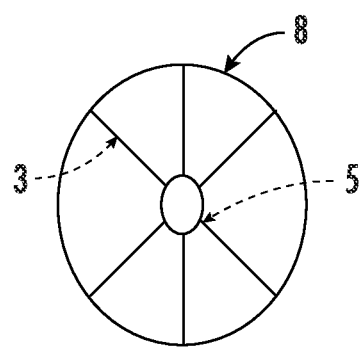
FIG. 4B is a cross-sectional view of the device of FIG. 4A.
Figure 5:
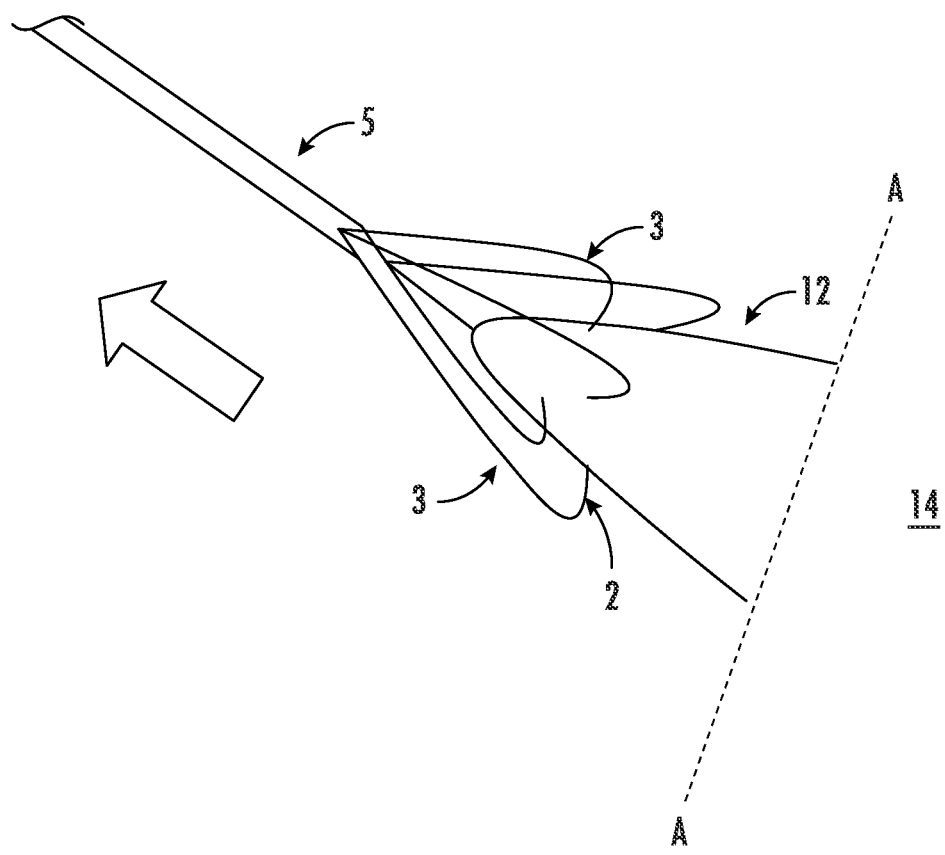
FIG. 5 is a schematic view of a device in one embodiment of the invention, as engaged with the wall of a bodily lumen.

As shown in FIGS. 2 and 5, central apparatus 5 is disposed through catheter 11 and is attached at its proximal end (preferably releasably) or through a bore (not shown) disposed axially through central apparatus 5 to a pusher structure 9. As shown in FIGS. 1 and 4, four or six arms are present; however, it will be apparent to those of ordinary skill in the art that a lesser or greater number of arms may be utilized; e.g., from at least 2 up to 20 arms, preferably 4-12 arms, most preferably 4-8 arms. FIGS. 1B and 4B also depict the optional shell cover 8 disposed over arms 3.

Pusher structure 9 is shown in phantom in FIGS. 2 and 5 as a guidewire, but may be any equivalent structure, such as a rod or catheter. If a guidewire, pusher 9 may be a conventional wire or a self-centering guidewire, to facilitate insertion of the closure device through a perforation. Where a self-centering guidewire is utilized, the tissue capture structure defined by arms 3 of device 1 need not be as large in diameter as compared to the diameter of the perforation being treated. In either embodiment, central apparatus 5 and pusher 9 are insertable through a catheter 11 for an endoscope 13.

As noted, in surgical use, the device is inserted into catheter 11 in its compressed configuration. Tension exerted by contact between the inner diameter of catheter 11 against arms 3 retains them in a downward attitude, compressed toward and along the elongated central axis 15 of device 1. Endoscope 13 is advanced to the site of the perforation to be treated in a body cavity and loader catheter 11 advanced through the perforation across line A-A', as shown in FIG. 2 or adjacent the perforation as shown in FIG. 5. The closure device is advanced distally out of loader catheter 11, by operation of pusher apparatus 9. As the arms 3 are advanced distally out of loader catheter 11, arms 3 resiliently deploy into the expanded configuration as the tension on arms 3 is released. As such, the arms 3 do not become fully deployed from the proximal end of the loader catheter until they have passed completely out of the loader catheter and through the perforation. Loader catheter 11 is then retracted.

Figure 3:
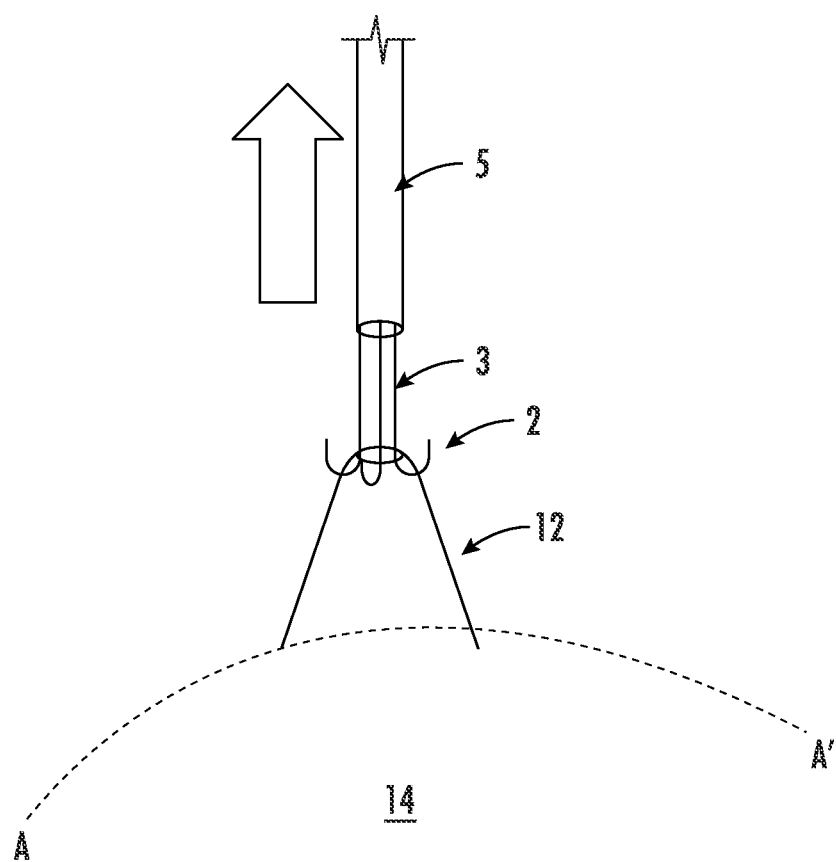
FIG. 3 is a schematic view of a device in one embodiment of the invention, as engaged with the wall of a bodily lumen.

Once arms 3 are fully deployed in an expanded configuration, device 1 is pulled back toward the perforation (in the direction indicated by the block arrow of FIG. 3) until the hooks are captured into the tissue surface of the organ wall 12 around the perforation site. Arms 3 then become everted out of the intraluminal space 14 through the perforation along line A-A' by retraction of the central apparatus toward and back through the perforation. As device 1 is pulled backward, arms 3 and hooks 2 exert a pulling force on the serosal/adventitial surface 12, everting it into the luminal space. The orientation of hooks 2 facilitates perforation of the tissue by hooks 2 upon exertion of a pulling force. When configured as an acquisition device, the tissue capturing structure is advanced out of the catheter and expanded depending on the targeted lesion (e.g. precancerous mucosa or bleeding ulcer). Once the lesion is secured by hooking the site, the tissue capturing structure is then closed around the lesion by retracting the arms into the lumen of the catheter while the catheter remains stationary. However, it will be apparent to those of ordinary skill in the art, that alternative embodiments are possible in which the tissue capturing structure is closed around the lesion and tissue is approximated by moving the arms into the lumen catheter via movement of the catheter toward the bodily opening while the arms remain stationary.

Within the context of this application the terms memory shape materials and/or polymers and/or alloys, nitinol and/or super-elastic materials may be used interchangeably to refer to as materials capable of employing, shape memory where the materials may be deformed from an original, heat-stable configuration, to a second, heat-unstable configuration. The article is said to have shape memory for the reason that, upon the application of a trigger, for example heat, it can be caused to revert, or to attempt to revert, form its heat-unstable configuration to its heat-stable configuration therein it "remembers" its original heat-stable configuration or shape.

The device of the present invention overcomes the deficiencies of the background art by providing a tissue closure device that may be anchored with a plurality of arms having tissue anchoring structures and wherein closure is achieved without folding the tissue anchors within the tissue to achieve closure, while providing sufficient radial force to close a tissue site. The device includes a plurality of arms seamlessly extending out of the distal end of a delivery tool. As illustrated throughout the Figures, the device may be configured such that the arms have a plurality of transitional configurations, for example 2, 3, 4, or more transitional configurations.

In various embodiments, the tissue capturing structure of the device according to the present invention is provided from super-elastic materials and/or memory shape polymers, shape memory alloys, plastics or alloys and materials capable of super-elastic and/or memory shape properties and having a plurality of stable configurations. Such materials and/or alloys or polymers thereof may include, but are not limited to Ni—Ti, Ni—Ti alloys, nitinol, Cu based alloys, Cu—Zn—Al, Au—Cd, Ni—Al, stainless steel 316, polymers, BeCu alloy, CoCr alloy, Ag—Cd, Au—Cd, Cu—Al—Ni, Cu—Sn, Cu—Zn, Cu—Zn—Si, Cu—Zn—Sn, Fe—Pt, Mn—Cu, Fe—Mn—Si, Pt alloys, Co—Ni—Al, Co—Ni—Ga, Ni—Fe—Ga, Ti—Pd, Ni—Ti—Nb, Ni—Mn—Ga, and the like as is known in the art and/or any combination thereof. In various embodiments, preferred materials for use in the arms of the device of the invention are shape memory materials, such as nitinol. Nitinol is a "shape memory alloy" based on nickel and titanium with moderate deformability. Other shape memory materials having greater deformability may also be utilized, so long as (1) the arms of the closure device may be moved from a compressed state to an expanded state as described herein; and (2) the tissue anchoring structures of the arms are sufficiently rigid to engage and remain secured in tissue when subjected to pulling or pushing forces according to the invention.

In some applications, the tissue anchoring structures may be detached and left behind in the tissue. For such applications, the material used at least in the tissue anchoring structures, may be a polymer with bioresorbable, thermoplastically deformable shape memory characteristics, such as those described in U.S. Patent Publication No. 2010/0262182 (herein incorporated by reference in its entirety), or a biological material, such as collagen. In the latter embodiments, the supporting arms may be formed of the same material as the tissue anchoring structures (e.g., barbs or hooks), or a different material. They may also be treated with molecules known in the art to promote epithelialisation and wound healing (e.g., chitosan, steroids and the like).

If present, the shell cover may be of any biocompatible material including, for leave behind applications, a bioabsorbable material (shape memory or not), such as polylactic acid (PLA), poly-glycolic acid (PGA), polylactide-co-glycolide, isomers and combinations thereof. The shell cover may also be formed of a biological material (e.g., collagen).

As discussed herein, the invention provides a system which includes the device of the disclosure in combination with a catheter or scope device and optionally a closure device operable to close a bodily opening. As used herein, a closure device for use in the system of the invention is intended to includes any device which is capable of, or facilitates, closure and/or sealing of a bodily opening. In some embodiments, the closure device is a ligation band, a tissue clip, a suture or a staple. In one embodiment, the closure device is a band ligator. In some embodiments, the closure device is operable to close or seal the bodily opening via application of radiation, such as visible light, infrared radiation, microwave radiation, radio waves, very low frequency (VLF) radiation, extremely low frequency (ELF) radiation, and thermal radiation. In some embodiments, the closure device is operable to close or seal the bodily opening via application of a bioadhesive or pharmaceutical agent, such as a biomolecule, protein, oligonucleotide, hormone, steroid, growth factor, transcription factor, cell, matrix protein, chemical compound, or combination thereof.

Approximation of the edges of the tissue surrounding a bodily opening closes the opening and provides a treatment surface for sealing of the perforation. As discussed above, sealing can be accomplished by band ligation or by application of a clip, suture or staple to the tissue. Alternatively, sealing may be accomplished by application of energy to the tissue (causing tightening of tissue collagen; e.g., by operation of one or more radiofrequency, RF, electrodes disposed on arms 3 or introduced to the treatment site through endoscope 13) or by application of a biocompatible surgical adhesive. Similarly, resection of tissue acquired by the device may be performed using known surgical methods, followed by sealing the tissue as necessary.

The device of the present invention offers unique advantages as compared to conventional devices. One advantage is that precise placement of the device is not critical therefore the closure can be performed quickly without specialized training. Additionally, the device can be customized to be used for small or large perforations unlike convention devices which have limits on the size of the perforation.

Figure 6:
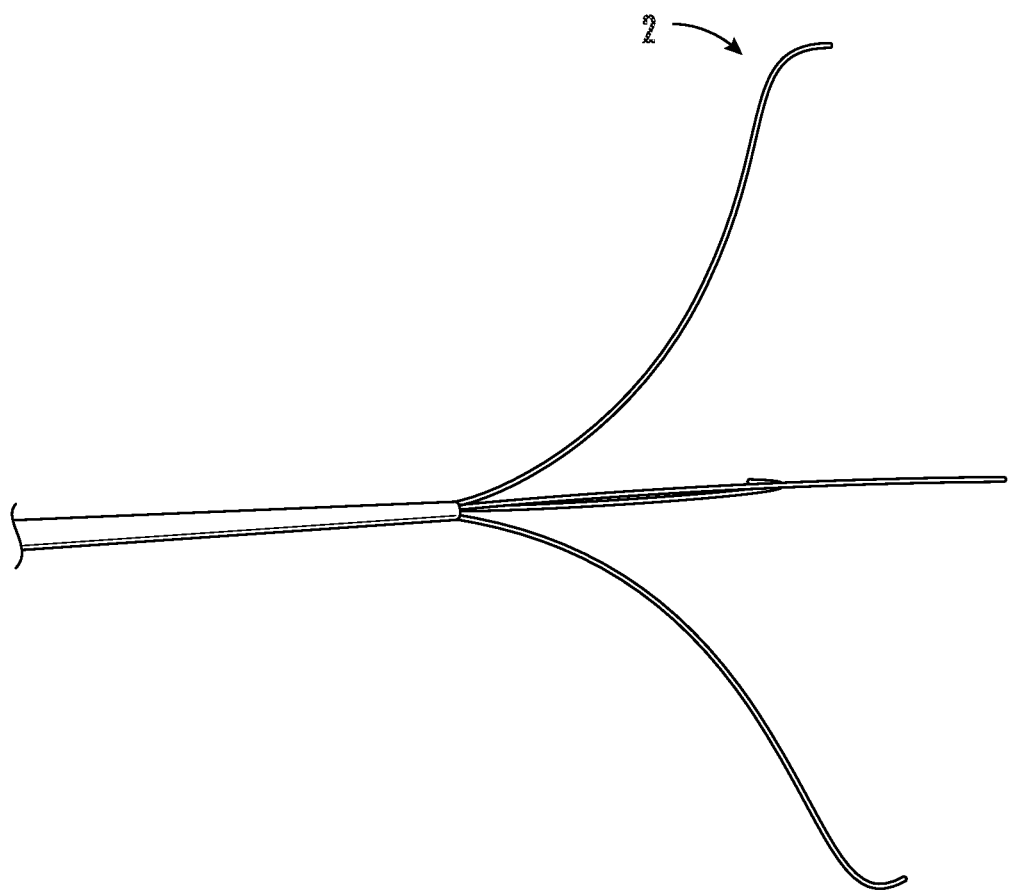
FIG. 6 is a schematic view of the device in one embodiment of the invention, in an expanded state with forward facing hooks.
Figure 7:
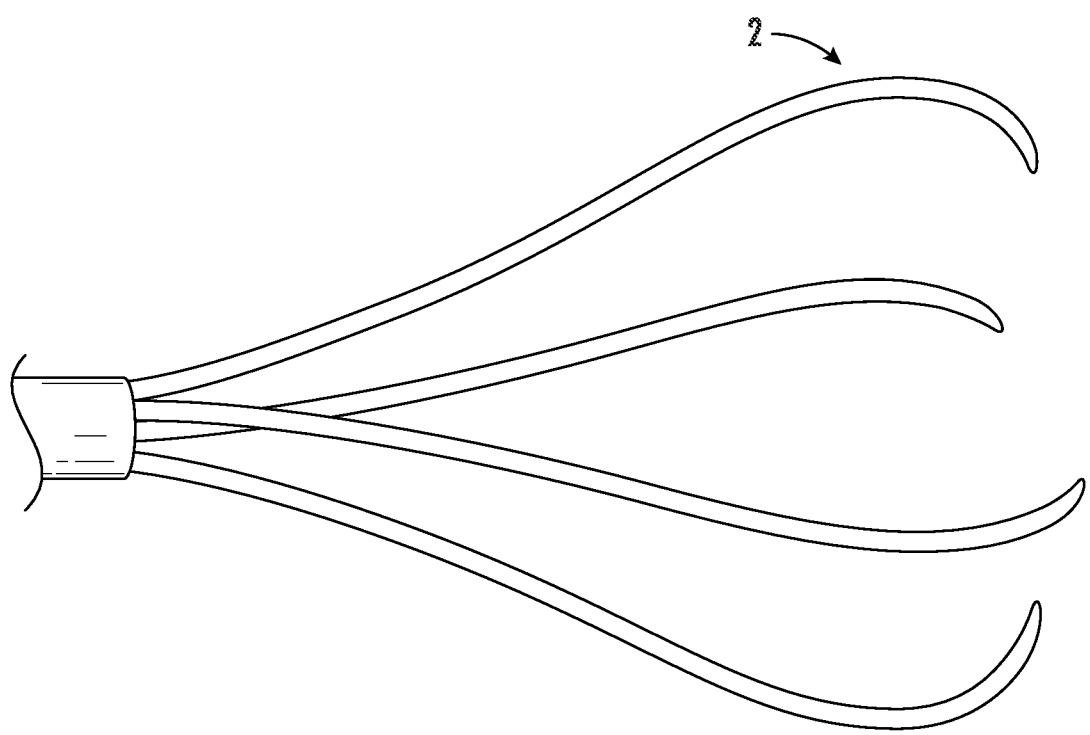
FIG. 7 is a schematic view of the device in one embodiment of the invention, in a partially expanded state with forward facing hooks.

With reference to FIGS. 6 and 7, in embodiments, the device may include forward facing hooks 2. Reverse hooks typically require that the delivery catheter cross the bodily perforation and engage tissue blindly on the opposite side of the perforation. As such, tissue engagement cannot be directly visualized with an endoscope. Use of forward facing hooks as shown in FIGS. 6 and 7 allow for direct visualization through the endoscope, while engaging the tissue during deployment.

In various embodiments, the device may include a combination of forward facing hooks and reverse facing hooks. For example, the device may be configured such that forward facing hooks are disposed on one side of the perforation (outside of the perforation) and reverse hooks disposed on the opposing side of the perforation (through the perforation) such that tissue is pinched between the tips of the hooks on opposing sides of the perforation.

Many of the devices depicted throughout the Figures include tissue anchoring structures configured as hooks. However, it will be apparent to those of ordinary skill in the art that tissue anchoring structures may be configured in a variety of shapes. For example, tissue anchors may be shaped in an arrow-head like and/or barb configuration, about the distal end of the anchors. Preferably tissue anchor shape provides for securely anchoring and/or embedding the device within a given tissue.

Figure 8A:
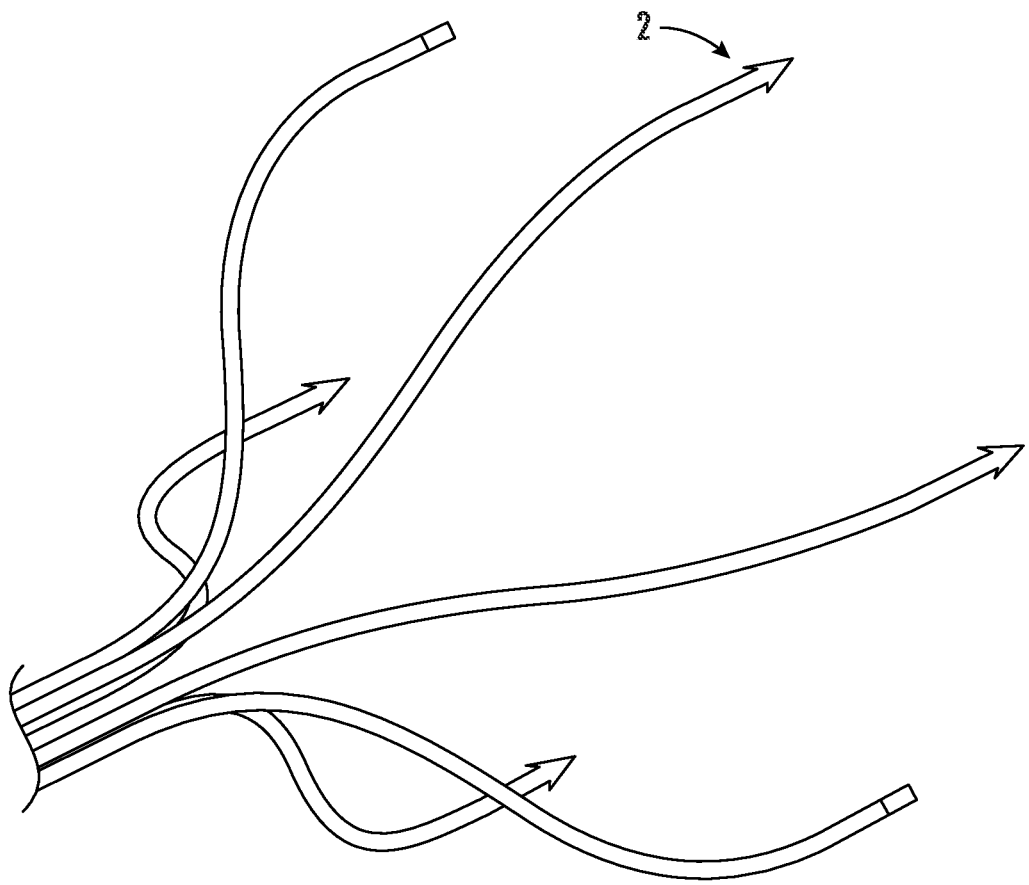
FIG. 8A is a schematic view of the device in one embodiment of the invention, in an expanded state with forward facing double barbed hooks.
Figure 8B:
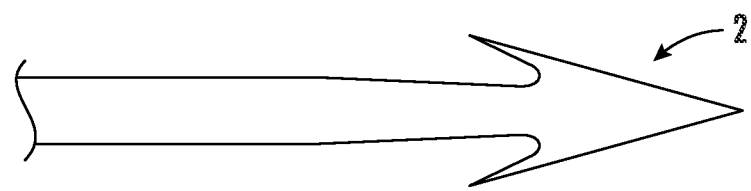
FIG. 8B is an expanded view of a double barbed hook of the device of FIG. 8A.

In embodiments, the device includes single or double barbed (e.g., arrowhead shaped) hooks as shown in FIGS. 8A and 8B. The barb feature (either single or double) helps to retain the tissue after engagement. In the case of a single barb, if a bias force is applied to the hooks, it is possible for the tissue to slide over the barb and disengage. A double barb adds security and continues to retain the tissue regardless of whether a lateral force is applied.

Figure 9A:
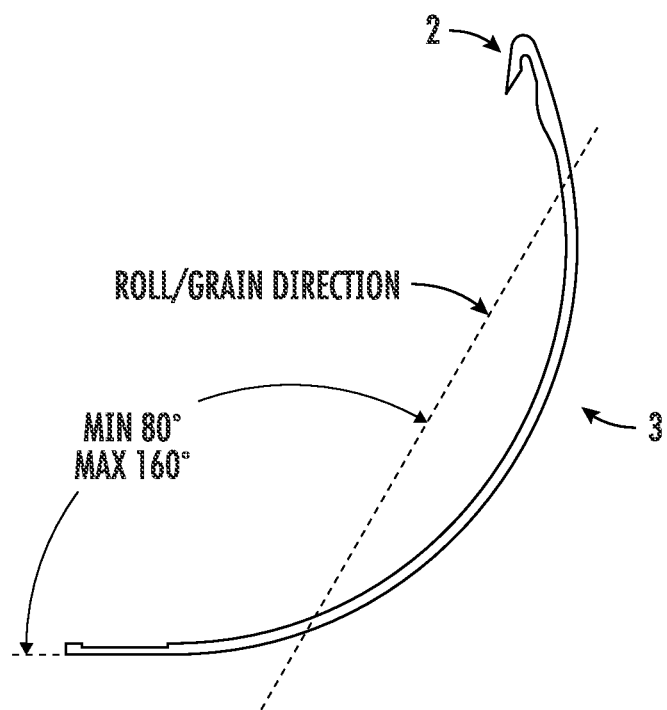
FIG. 9A is a schematic view of an individual arm of a device in one embodiment of the invention, in an expanded state.
Figure 9B:
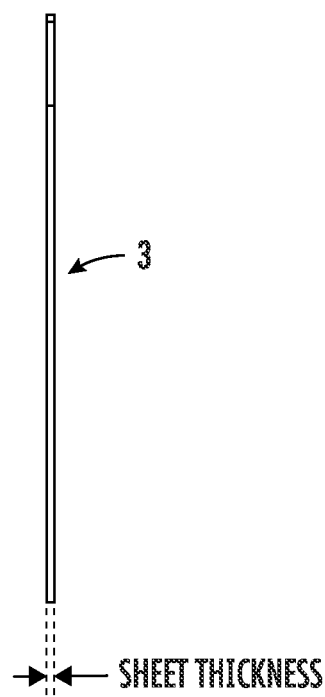
FIG. 9B is a side view of the individual arm of FIG. 9A.

In embodiments, the device includes one or more arms 3 as shown in FIGS. 9A and 9B which have a tissue anchor structure 2 shaped as a hook. Ideally, the arm is manufactured from a flat stock, e.g., flat sheet of material (as opposed to round wire), such as nitinol, by laser cutting for example. Hooks manufactured from round wire limit the ability to add features and customize geometry. Hooks cut from a flat sheet allow for an extra dimension of design. Features can easily be incorporated to improve overall geometry, the ability to puncture tissue, as well as collapse into the catheter and assembly. In embodiments, the arm and tissue anchoring structure have a thickness (sheet thickness as shown in FIG. 9B) of from about 0.5 mm to about 3 mm.

Figure 10:
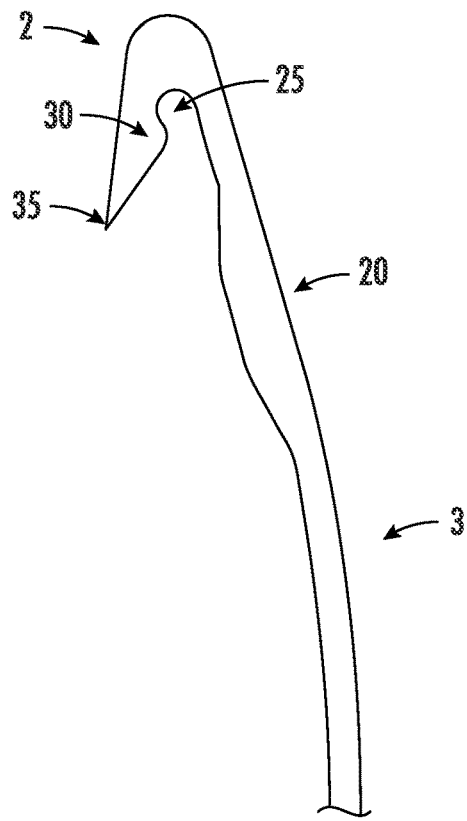
FIG. 10 is a schematic view of a distal region of an arm of a device in one embodiment of the invention.
Figure 11:
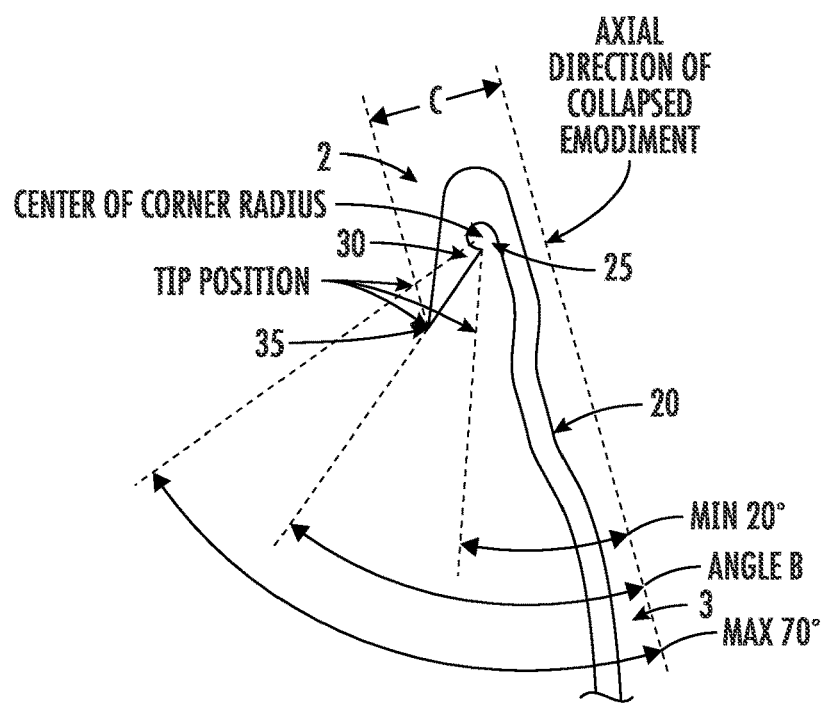
FIG. 11 is a schematic view of a distal region of an arm of a device in one embodiment of the invention.

In embodiments, the device includes one or more arms having a centralizing feature on the distal region of the arm as the arm transitions to the tissue anchoring structure. For example, FIGS. 10 and 11 show a distal region of arm 3 including a tissue anchoring structure in the shape of a hook 2. Proximal to the hook 2 is centralizing region 20 which is characterized by an increase in arm diameter as the arm transitions into the hook 2 structure (FIG. 10), or an increase in arm diameter as the arm transitions into the hook 2 structure which has been back-cut to maintain a constant arm diameter but which imparts alternating arc transitions in the arm (FIG. 11). Addition of the centralizing 'ramp' feature 20 (region of increased arm diameter as compared to the diameter of the proximal region of the arm) allows for the arms and hooks to collapse to a tighter inner diameter (ID) lumen than would normally be allowed by the ID of the distal tip alone. It also provides tactile feedback to let a user operating the device know when the arms are fully retracted with a catheter. The back-cut incorporated into the centralizing feature 20 allows for more flexibility of the distal region of the arm, which allows for shape change (and tip-entry angle) during tissue engagement.

In embodiments, the device includes one or more arms having tissue anchoring structures which include a keyhole feature on one or more of the tissue anchoring structures. FIGS. 10 and 11 show a distal region of arm 3 including a tissue anchoring structure in the shape of a hook 2 which includes a keyhole feature 25 which is characterized by a generally circular or curved void or recess defining a recess which can accommodate tissue engaging the hook. The more tissue that is captured around a perforation, the better the chance of successful band ligation. The addition of keyhole feature 25 allows for more tissue to be engaged by the hooks. In embodiments, the keyhole feature is customized in size to accommodate different target anatomies (i.e., the stomach is a thicker wall organ and requires a larger keyhole). Use of a hook tip having a rounded transition 30 between the keyhole 25 and the hook tip 35 as shown in FIG. 10, allows disengagement (if necessary) to be easier. Incorporation of a barb or non-rounded transition 31 between the keyhole 25 and the hook tip 35 as shown in FIG. 11, acts to secure the tissue in place to help prevent accidental disengagement of tissue if the catheter is inadvertently advanced.

Figure 12:
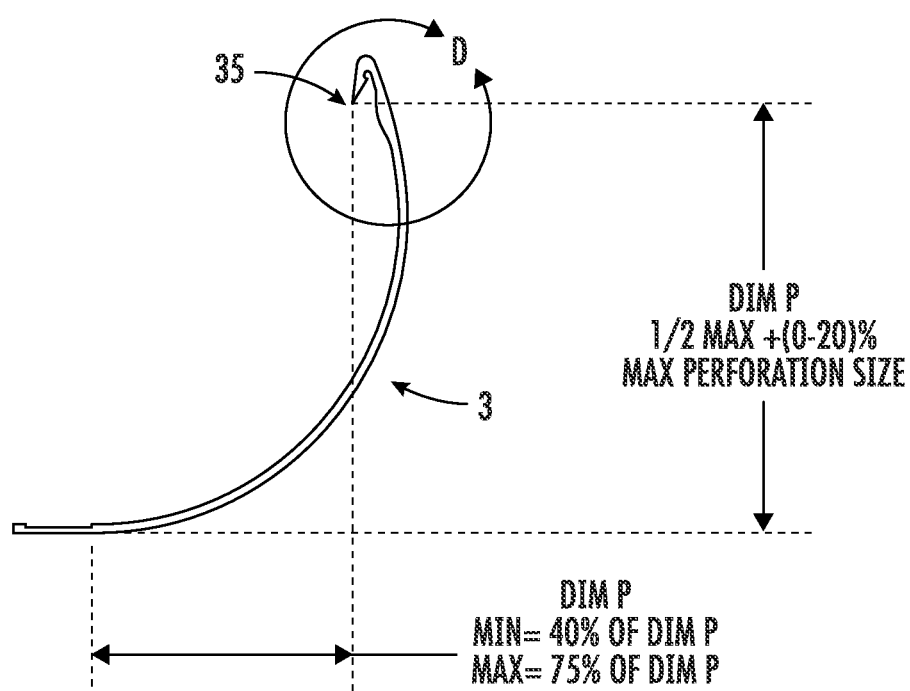
FIG. 12 is a schematic view of an individual arm of a device in one embodiment of the invention, in an expanded state.

In embodiments, the device includes one or more arms having a specifically defined arc length. A specific range of arc lengths allows for the optimum volume of tissue to be captured into the band ligation device of the system. If the arm is too short, not enough tissue is captured. If the arm is too long, too much tissue can be engaged which can be difficult to collapse. Furthermore, longer arms require more room in the anatomy to deploy. FIG. 12 illustrates an arm having a specifically defined arc length and depicts a specific formula for determining arc length based on perforation diameter. Ideally, the arc length (defined as the distance from the central axis to a radially expanded hook tip) of arm 3 extends up to or slightly greater than ½ the maximum perforation diameter or length (noted as Dimension P in FIG. 12). The arc distance of the arm 3 (defined as the distance from the distal central apparatus to the perpendicular intersection of a radially expanded hook tip with the central axis) is between about 40-70 percent of Dimension P (noted as Dimension D in FIG. 12).

In embodiments, the overall diameter of the expanded tissue capturing structure is from about 5 to 100 mm, or about 10 to 50 mm, or about 10 to 30 mm.

In embodiments, the overall length of an arm from the central apparatus to the distal tip of the tissue anchoring structure is between about 5 to 100 mm, or about 10 to 50 mm, or about 10 to 30 mm.

In embodiments, the device of the invention includes one or more arms having a specifically defined angle determining tip entry when engaging tissue upon expansion. This angle is denoted as angle β (beta) in FIG. 13. If the tip entry angle is too acute or too obtuse, it is difficult to engage the tissue. Ideally, angle β is found to be optimum when the angle allows the tissue piercing tip to enter tissue at an angle of about 90 degrees with respect to the plane of the tissue. In one embodiment, angle β is between about 50 to 120 degrees. In one embodiment, angle β is between about 70 to 100 degrees. In one embodiment, angle β is between about 55-60, 60-65, 65-70, 70-75, 75-80, 80-85, 85-90, 90-95, 95-100, 100-105, 105-110 or 110-115 degrees.

Figure 13:
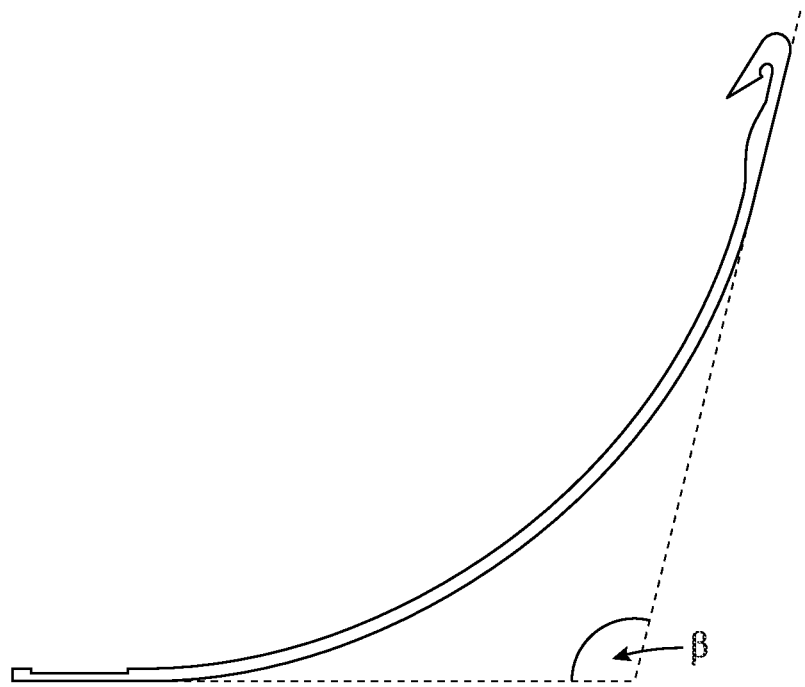
FIG. 13 is a schematic view of an individual arm of a device in one embodiment of the invention, in an expanded state.
Figure 14:
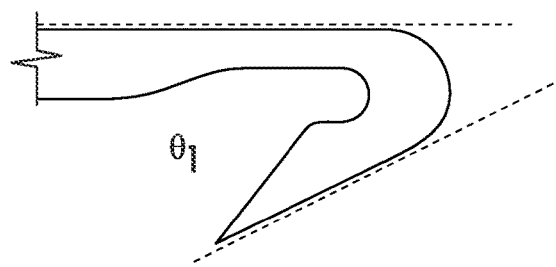
FIG. 14 is a schematic view of a tissue anchoring structure of a device in one embodiment of the invention.
Figure 15:
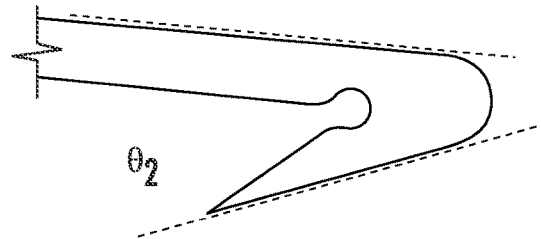
FIG. 15 is a schematic view of a tissue anchoring structure of a device in one embodiment of the invention.

In embodiments, the device of the invention includes one or more hook shaped tissue anchoring structures as shown in FIG. 13 or 14 which have specifically defined hook angles θ. In one embodiment, hook angle θ is between about 20 to 70 degrees. In one embodiment, hook angle θ is between about 20-25, 25-30, 30-35, 35-40, 40-45, 45-50, 50-55, 55-60, 60-65 or 65-70 degrees.

Figure 16:
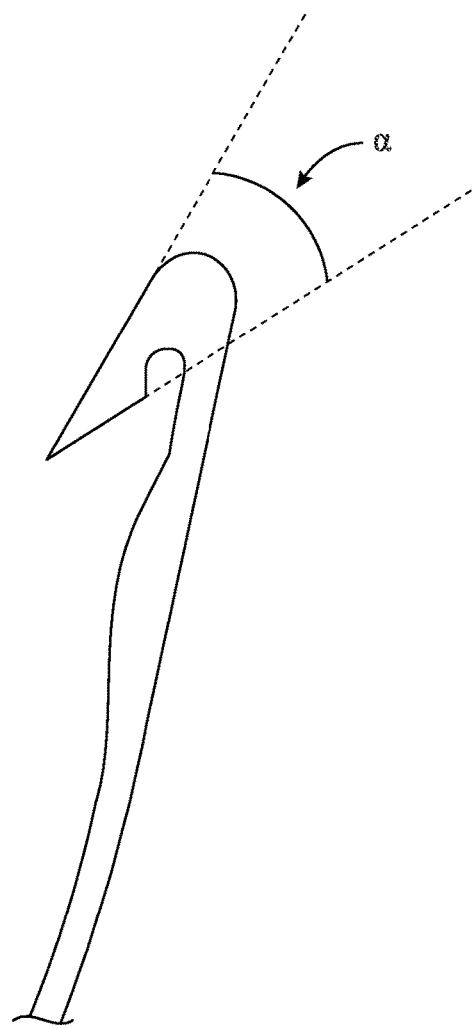
FIG. 16 is a schematic view of a tissue anchoring structure of a device in one embodiment of the invention.

In embodiments, the device of the invention includes one or more tissue anchoring structures which have specifically defined tissue penetrating tip angles (defining sharpness). FIG. 16 shows a tissue anchoring structure having a tissue penetrating tip angle α. In one embodiment, tissue penetrating tip angle α is between about 10 to 70 degrees. In one embodiment, tissue penetrating tip angle α is between about 10-15, 15-20, 20-25, 25-30, 30-35, 35-40, 40-45, 45-50, 50-55, 55-60, 60-65 or 65-70 degrees.

Figure 17A:
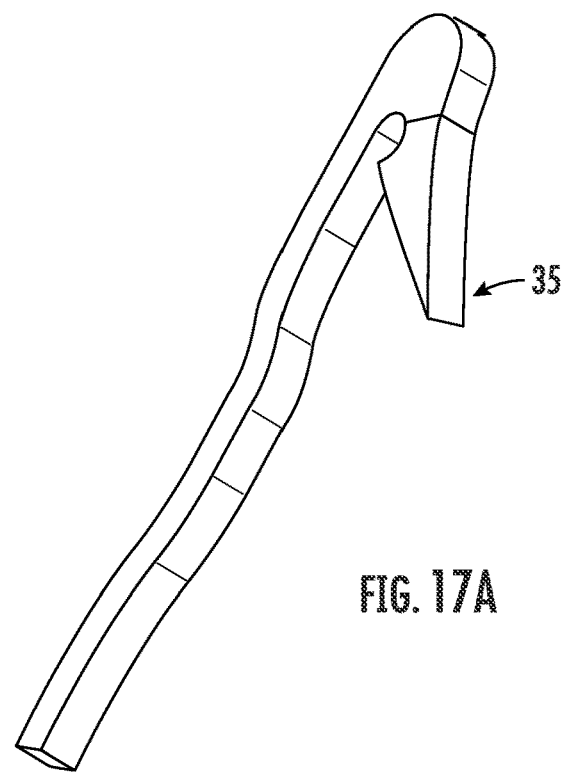
FIG. 17A is a perspective view of a tissue anchoring structure of a device in one embodiment of the invention.
Figure 17B:
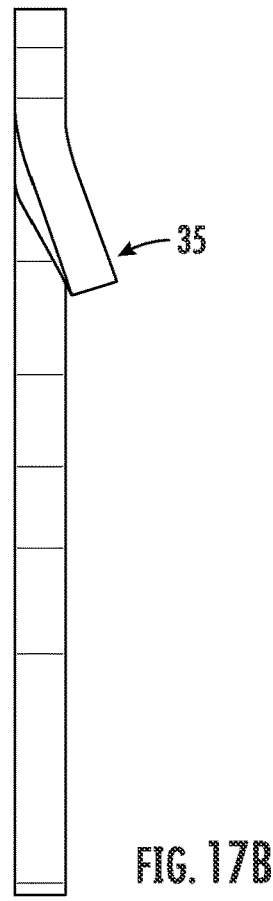
FIG. 17B is a side view of the tissue anchoring structure of FIG. 17A.

In order to successfully band ligate a perforation, a sufficient amount of tissue must be captured. In certain cases, simply collapsing and withdrawing the hooks does not capture enough tissue. The inventors have developed a technique to capture additional tissue and assist the collapse of the tissue into the band ligation device. Specifically, rotating tissue anchoring structures, such as hooks allows a larger volume of tissue to cinch up into a smaller volume. A risk with this technique is bending the hooks and/or tissue disengagement of the hooks. As shown in FIGS. 17A and 17B, a bias can be placed on the hook and/or the hook tip 35 to allow for rotation to be applied in one direction that will enhance tissue security and minimize tissue disengagement and hook damage. In embodiments, the tip of the hook is offset at an angle relative to the longitudinal axis of the arm of between about 0-5, 5-10, 10-15, 15-20, 20-25, 25-30, 30-35, 35-40 or 40-45 degrees.

Figure 18A:
FIG. 18A is a schematic view of a device in one embodiment of the invention.
Figure 18B:
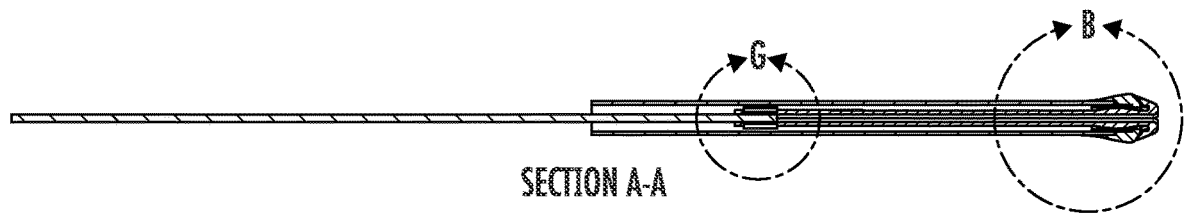
FIG. 18B is a cross-sectional view of the device of FIG. 18A along line A-A.
Figure 18C:
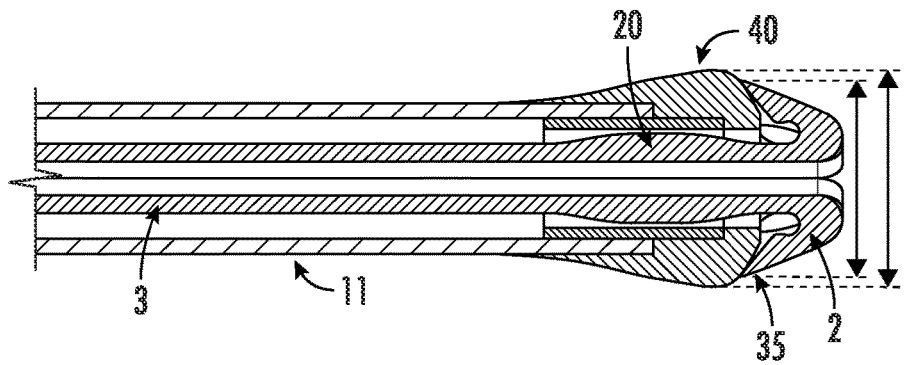
FIG. 18C is an expanded view of Detail B of FIG. 18B.

With reference to FIGS. 18A to 18D, the system may include a centralizing feature on the catheter or scope device. FIG. 18C shows a system in one embodiment of the invention that includes centralizing feature 40. The device is depicted in a compressed state with arms 3 fully retracted with the catheter 11 lumen. The centralizing feature 40 disposed on the distal tip of the catheter 11 has two functions. Firstly, the inner diameter (ID) of centralizing feature 40 accommodates centralizing region 20 and facilitates the collapse of the hooks 2 in a controlled, smooth manner. Secondly, the outer diameter (OD) of centralizing feature 40 registers the hook tips 35 to keep them concentric with the longitudinal axis of the delivery system; it also protects the hook tips 35 from damaging the ID of the catheter or scope device.

Figure 18D:
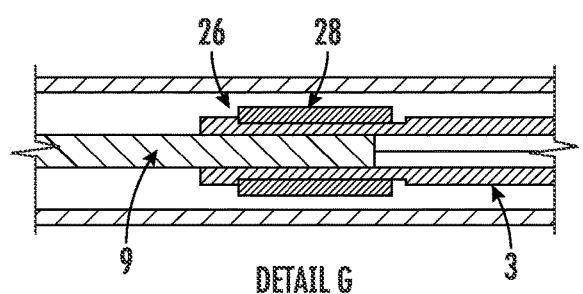
FIG. 18D is an expanded view of Detail G of FIG. 18B.
Figure 18E:
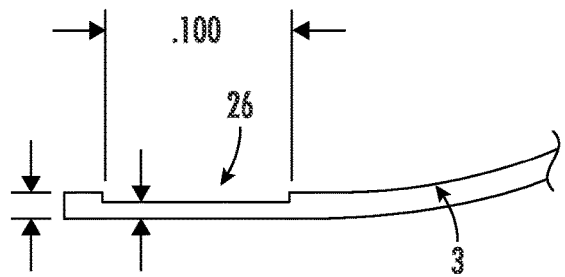
FIG. 18E is an expanded view of the distal region of an arm shown in FIG. 18D.

As also shown in FIGS. 18A to 18D, in embodiments, the system includes an arm retention feature. As shown in FIG. 18D, channel 26 is incorporated into the proximal end of the arms 3 which accommodates a weld ring 28 which attaches the arms to rod 9. This assembly forms the central apparatus. To install the weld ring, rod 9 is inserted into the ID of the arms 3 which physically secures ring 28 within channel 26. The arms are then welded to the rod 9. If a single arms weld fails, the arm continues to be retained by the ring 28 and cannot separate from the delivery system. This minimizes patient risk by minimizing the risk of components being left in the body. FIG. 18E illustrates channel 26.

Figure 19:
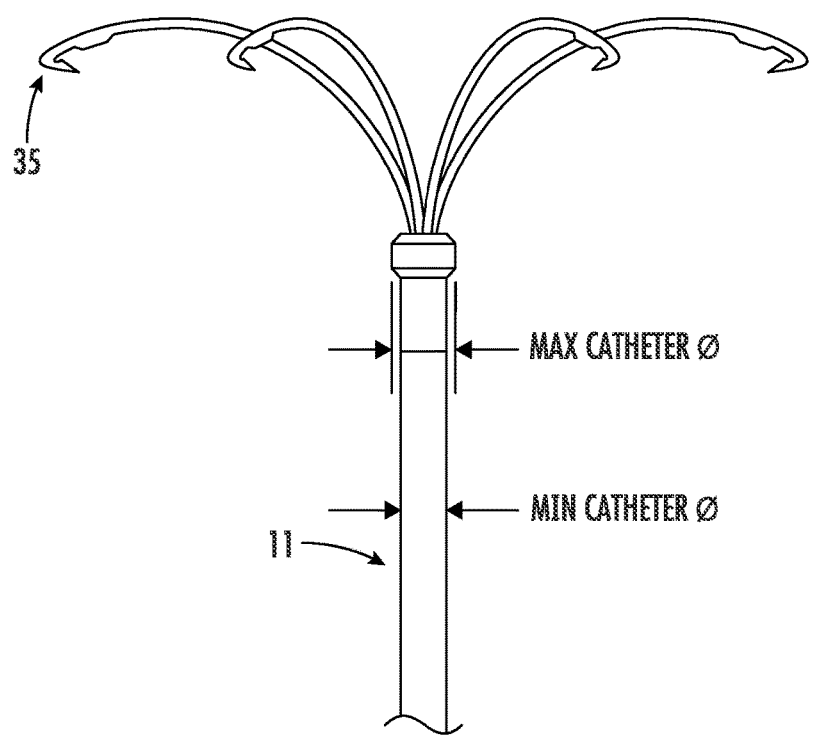
FIG. 19 is a schematic view of a system in one embodiment of the invention.
Figure 20:
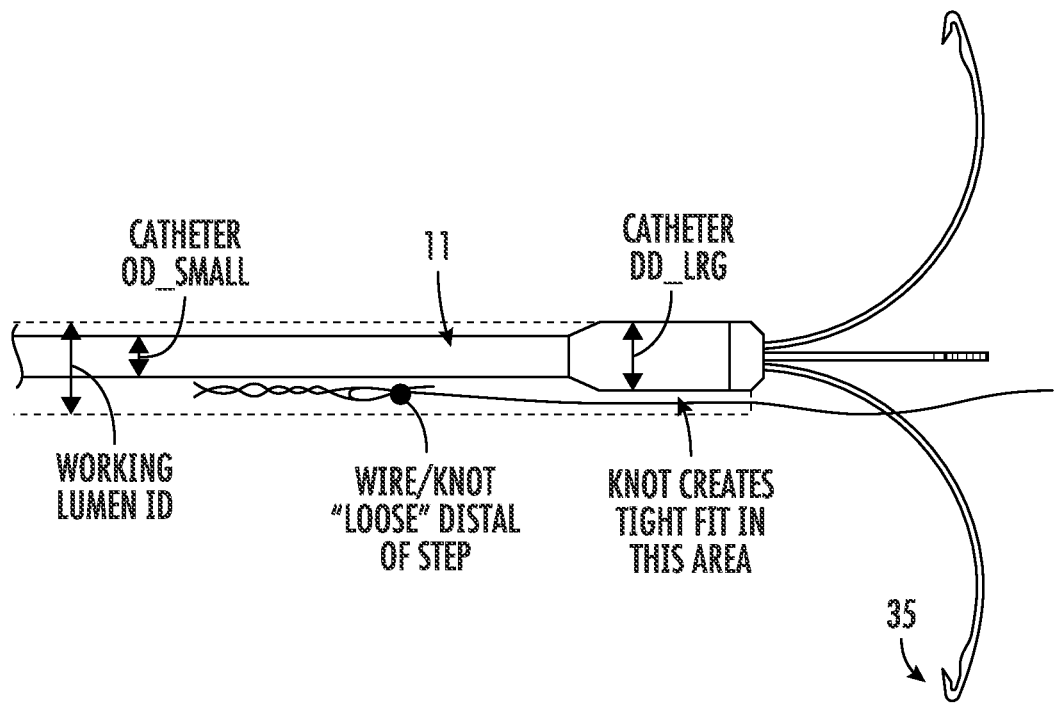
FIG. 20 is a schematic view of a system in one embodiment of the invention.

With reference to FIGS. 19 and 20, in embodiments, the system includes a stepped outer diameter (OD) on the delivery device. In the embodiment shown in FIGS. 19 and 20, the delivery device is catheter 11. The distal end of the catheter is enlarged to encapsulate and protect the hook tips 35, while the proximal side of the catheter has a smaller OD, and allows space for tether and knot embodiments utilized by current banding systems.

Figure 21:
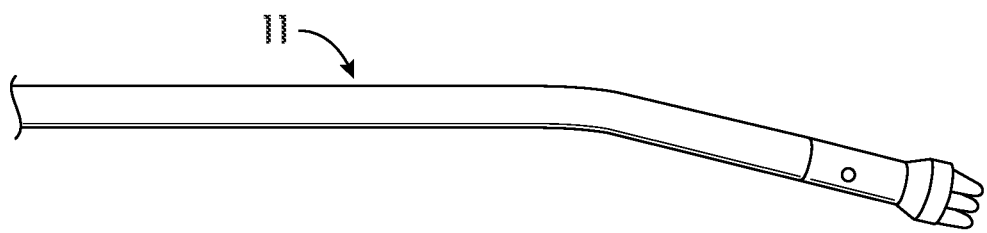
FIG. 21 is a schematic view of a system in one embodiment of the invention.

In embodiments where the system utilizes a catheter or scope device in which the working lumen utilized to deploy the device of the invention is not concentric to the closure device, i.e., the band ligator, upon collapse of the arms into the closure device, the hook tips may catch on the distal end of the closure device. To remedy this problem, in various embodiments, the delivery catheter or scope device may be articulating or include a permanent bend or angle as shown in FIG. 21. Incorporating a bend or curvature on the distal end of the delivery system allows the user to rotate and bias the deployed hook tips away from the edge of the banding system.

Figure 22:
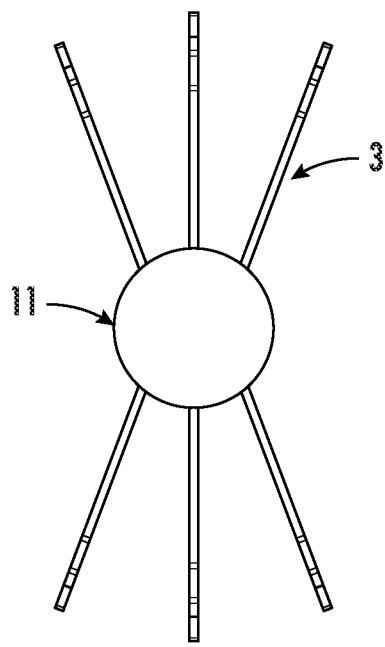
FIG. 22 is a front end view of a system in one embodiment of the invention having arms arranged asymmetrically spaced about the central axis.
Figure 23:
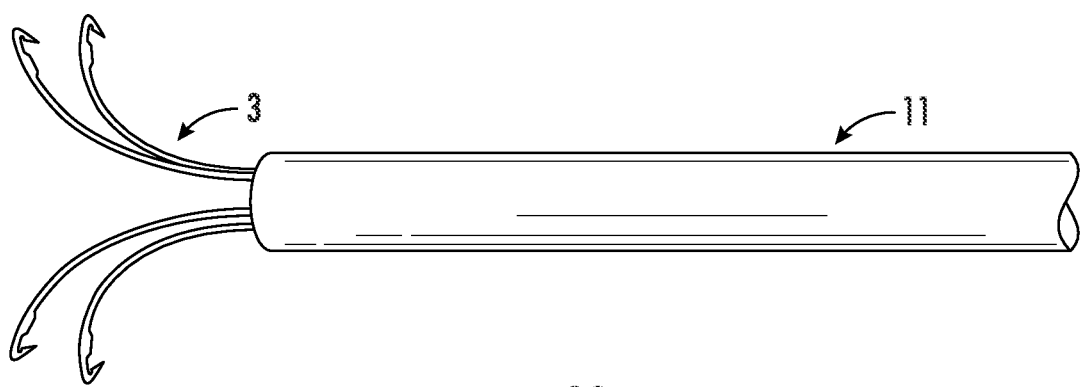
FIG. 23 is a schematic view of a system in one embodiment of the invention, wherein the radius of curvature varies between arms (asymmetric radius of curvature).
Figure 24:
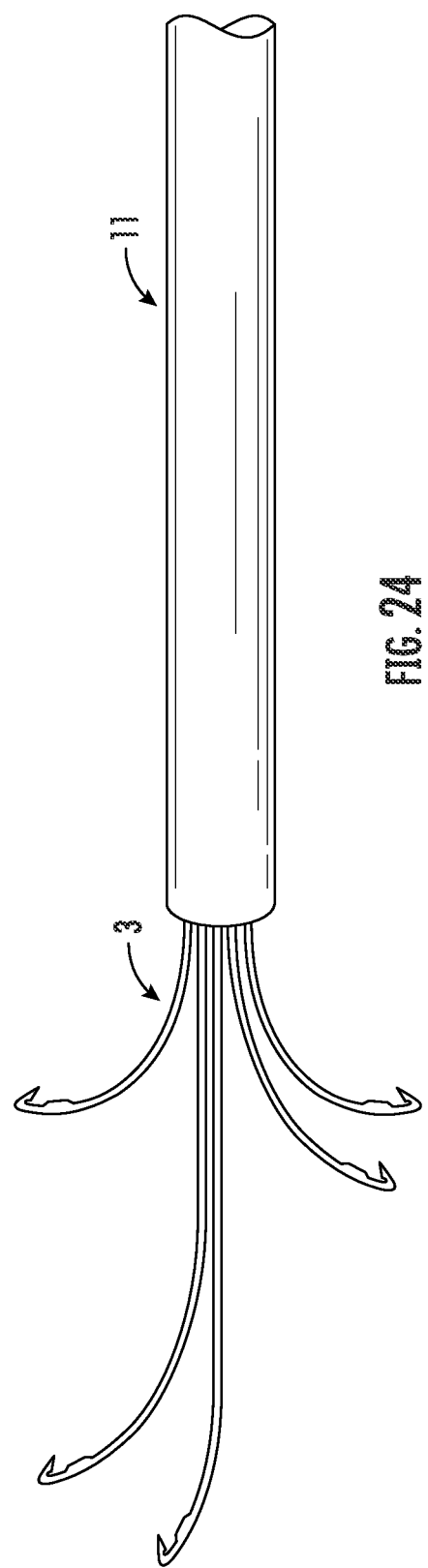
FIG. 24 is a schematic view of a system in one embodiment of the invention, wherein the arms are of different lengths (asymmetric arm length).

As will be appreciated by one in the art, the arms of the device of the invention may be arranged in any number of ways. FIGS. 22-24 illustrate different embodiments in which the arms are arranged asymmetrically. FIG. 22 depicts an embodiment in which the arms are spaced asymmetrically about the central axis. FIG. 23 depicts an embodiment in which the radius of curvature for each arm can be different. In this embodiment, a first pair of arms have a first radius of curvature, and a second pair of arms has a second radius of curvature different than the first. FIG. 24 depicts an embodiment in which different arms have different lengths. In this respect, the device may include combinations of arms having different expanded lengths. The arms may be expanded individually or in different groups to achieve different lengths. It will understood the device may include arms having different combinations of the features shown in FIGS. 22-24. For example, a device may include arms which are spaced asymmetrically about the central axis (FIG. 22) and the arms may be have two or more different radius of curvature (FIG. 23) and/or be of different lengths (FIG. 24).

In various embodiments, the system may include a mechanical component for transitioning the device between the compressed and expanded states. For example, the system may include an actuator controlling transitioning of the device, e.g., retraction or advancement of the arms out of and into the lumen of the delivery device. In one embodiment, the mechanical component may include a ratchet mechanism or slide mechanism operable by manual manipulation by a hand of an operator of the device. In various embodiments, the mechanical component may be disposed in the handle of the system.

To assist the operator in use of the device, the system may include a feature operable to inform an operator of status of device transitioning, for example, how far the device is deployed outside of the delivery device. In various embodiments, the feature is operable to provide a visual or audio measure of arm compression or expansion, e.g., length of deployment. In embodiments, the device includes a tactile indicator in the handle for hook collapse, created by bumps in hooks as discussed with regard to the embodiment of FIGS. 10 and 11 which include arms having centralizing region 20.

In embodiments, the device includes a visual marker on the distal end to indicate how far the device is advanced outside of the scope. The addition of a visual marker allows the user to know that when the marker becomes visible via the scope which indicates that the device is a particular distance (i.e., 1 cm) away from the closure device, i.e., the band ligator. The user can then better assess whether the device needs to be retracted or advanced further for procedural success.

As discussed herein the device of the invention provides a method for closure of a bodily opening. In practice, closure may be achieved by advancing a device or system of the invention into the bodily opening when device is in the compressed state. The device is then transitioned to a partially or fully expanded state thereby elongating one or more of the plurality of arms out of the lumen of the delivery device. Tissue is then captured via the tissue anchoring structures and the device is transitioned to the partially or fully compressed state to approximate tissue adjacent the bodily opening. The bodily opening may then be sealed using a closure device.

The device of the invention also provides a method for acquiring or resecting tissue at a target site, the method includes advancing a device or system of the invention to the target site in the compressed state.

The device is then transitioned to a partially or fully expanded state thereby elongating one or more of the plurality of arms out of the lumen of the delivery device. Tissue is then captured via the tissue anchoring structures and the device is transitioned to the partially or fully compressed state to approximate tissue adjacent the bodily opening. Tissue at the target site may then be resecting and any perforation sealed.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Illustrative Clinical Applications for Device

Intestinal Fistulas

Gastrointestinal fistulae most frequently occur as complications after abdominal surgery (7585%) although they can also occur as a result of underlying disease such as in patients with inflammatory bowel disease (IBD) such as diverticulitis or following radiation therapy and abdominal trauma. Fistula formation can result in a number of serious or debilitating complications, ranging from disturbance of fluid and electrolyte balance to sepsis and even death.

Endoscopic therapy represents a non-invasive way to treat this condition but has been hampered by limitations of the currently available devices. Use of the device disclosed herein is expected to overcome the limitations of the current devices to treat this condition.

Surgical Anastomotic Leaks

Surgical anastomotic leakage represents a major complication of gastrointestinal surgery, leading to increased post-operative morbidity. It is the commonest cause of death after intestinal resection. Early and optimal multidisciplinary management is based on three options: medical management, radiologic or endoscopic intervention, or surgical re-intervention. Prompt treatment should help decrease post-operative morbidity and mortality. With the rapid growth of bariatric surgery, the number of patients suffering with this condition is expected to increase.

Endoscopic therapy represents a non-invasive way to treat this condition but has been hampered by limitations of the currently available devices. Use of the device disclosed herein is expected to overcome the limitations of the current devices to treat this condition.

NOTES

NOTES is a technique in which surgical operations are performed within the body without a skin incision by using a natural body orifice to provide access. The principal challenge of transgastric NOTES procedures is still the feasibility and safety of access closure. The current devices all have limitations for closure of the incision for NOTES.

Use of the device disclosed herein has the potential to be the cornerstone for successful closure of the intestinal incision and be the foundation of moving NOTES into accepted clinical practice.

Bleeding Intestinal Lesions

Gastrointestinal bleeding is one of the most common reasons for hospitalization and a major cause of morbidity and mortality worldwide. Despite improvements in the management of this condition, the mortality rate has remained unchanged, possibly due to a longer life expectancy and the corresponding higher number of comorbidities. There are many endoscopic devices that have been used for endoscopic hemostasis. One technique is to secure the bleeding lesion within the endoscopic cap see below image. The limitation of this technique is that lesions can only be treated that are smaller than the size of the cap. Use of the device disclosed herein will overcome this limitation.

Endoscopic Mucosal Resection

One endoscopic technique for resection early cancer uses the endoscopic cap to capture the tissue which is ligated with a rubber band. Unfortunately the resection size is limited by the size of the cap. Use of the device disclosed herein will overcome this limitation.

Foreign Body Removal

An estimated 1500 people in the United States die annually from foreign bodies in the upper-gastrointestinal tract. Ingestion of foreign bodies is common, especially, among children who represent 80% of these emergencies. Most foreign body ingestions in children are coins, toys, magnets and batteries. Most foreign body ingestions in adults are related to eating, leading to either bone or meat bolus impaction. Current endoscopic removal devices are limited because of the diameter of the retrieval devices. Use of the device disclosed herein will overcome this problem.

Hernia Repair

Abdominal hernias may be formed in the abdominal wall due to heavy lifting, coughing, strain imposed during a bowel movement or urination, fluid in the abdominal cavity, or other reasons.

During hernia repair, a graft material such as a mesh or patch may be disposed to cover the perforation. The graft material may completely overlap with the perforation, and the edges of the graft material may at least partially overlap with tissue surrounding the perforation. The graft material then may be secured to the surrounding tissue in an attempt to effectively cover and seal the perforation. In order to secure the graft material to the surrounding tissue, sutures commonly are manually threaded through the full thickness of the surrounding tissue, then tied down and knotted. However, such manual suturing techniques are time consuming and/or difficult to perform. Use of the device disclosed herein will overcome this problem.

Vaginal Wall Repair Post Hysterectomy

Use of the device disclosed herein is expected to be capable of being used to effectively and efficiently repair organ wall defects.

Septal Defect Repair

Use of the device disclosed herein is expected to be capable of being used to effectively and efficiently repair septal defects.

Although the invention has been described with reference to the above examples, it will be understood that modifications and variations are encompassed within the spirit and scope of the invention. Accordingly, the invention is limited only by the following claims.

What is claimed is:

1. A device for facilitating closure of a bodily opening or acquiring tissue, the device having a compressed configuration and an expanded configuration and comprising:
    a) a tissue capturing structure having a plurality of arms elongated along a central axis, each arm terminating at a distal tip having a tissue anchoring structure, wherein the tissue anchoring structure comprises a hook, wherein the hook faces toward the central axis of the tissue capturing structure in the compressed state, wherein the hook comprises a barb, and wherein the arm comprises a centralizing ramp positioned immediately proximal to the hook to facilitate collapse of the arms and associated hook toward the central axis, and wherein the centralizing ramp comprises a first side and a second side, wherein the first side is closer to the central axis than the second side, and wherein the first side includes a portion that protrudes towards the central axis, such that the centralizing ramp is characterized by a portion of the arm where a distance between the first side and the second side of the centralizing ramp is greater than a distance between a first side and a second side of the arm proximal to a proximal end of the centralizing ramp; and
    b) a central apparatus disposed along the central axis securing the plurality of arms,
    wherein the plurality of arms expand radially from the central axis during transition from a compressed state to an expanded state, and
    wherein the device is operable to centralize and align the plurality of arms along the central axis when the device is in the compressed state.

2. The device of claim 1, wherein the distal tip of each arm is oriented toward the central axis when in the expanded state.

3. The device of claim 1, wherein the distal tip of each arm is oriented away from the central axis when in the expanded state.

4. The device of claim 1, wherein the plurality of arms comprise a first set of distal tips which are oriented towards the central axis, and a second set of distal tips which are oriented away from the central axis, when in the expanded state.

5. The device of claim 1, wherein the tissue capturing structure generally defines an umbrella shape or everted umbrella shape when in the expanded state.

6. The device of claim 1, wherein the tissue anchoring structure is configured to pierce tissue.

7. The device of claim 1, wherein the distal tip of the hook is offset relative to the central axis.

8. The device of claim 7, wherein the distal tip is offset relative to the central axis at an angle of between about 1 to 60 degrees.

9. The device of claim 7, wherein the angle is between about 1 to 45 degrees.

10. The device of claim 1, wherein the hook forms an angle of between about 5 to 50 degrees.

11. The device of claim 1, wherein the hook comprises a key-hole structure.

12. The device of claim 1, wherein the distal tip of each arm is generally perpendicular to the central axis in the fully expanded state, or form an angle of 90, 80, 70, 60, 50, 40, 30, 20, 10 degrees or less with respect to the central axis.

13. The device of claim 1, wherein the device comprises between about 2 to 20 elongated arms.

14. The device of claim 13, wherein the device comprises between about 4 to 8 elongated arms.

15. The device of claim 1, wherein the plurality of arms are formed of a deformably resilient shape memory material.

16. The device of claim 15, wherein the deformably resilient shape memory material is an alloy, polymer or combination thereof.

17. The device of claim 16, wherein the plurality of arms are formed of a deformably resilient shape memory alloy.

18. The device of claim 1, wherein the tissue capturing structure is formed of a bioresorbable material.

19. The device of claim 1, wherein the tissue capturing structure is treated to promote wound healing.

20. The device of claim 1, wherein the plurality of arms define a shape having a first diameter in the compressed state and a second diameter in the expanded state, wherein the second diameter is greater than the first diameter.

21. The device of claim 1, wherein the plurality of elongated arms are operably coupled to a pusher structure via the central apparatus to facilitate deployment of the device.

22. The device of claim 21, wherein the pusher structure is configured as a guidewire, rod or catheter.

23. The device of claim 22, wherein the pusher structure is a guidewire.

24. The device of claim 23, wherein the guidewire is self-centering.

25. The device of claim 21, wherein the pusher structure and the central apparatus are adapted to be insertable through a lumen of a catheter or an endoscope.

26. The device of claim 1, wherein a distal portion of the device is articulating.

27. The device of claim 1, wherein the device is operable to transition the plurality of arms individually or in unison.

28. The device of claim 1, wherein the plurality of arms have an expanded length that is variable.

29. The device of claim 28, wherein each arm has an expanded length that is the same.

30. The device of claim 28, wherein each arm has an expanded length that is different.

31. The device of claim 28, wherein the plurality of arms have an expanded length of two or more different lengths.

32. The device of claim 1, wherein the tissue capturing structure is configured such that tissue anchoring structures are disposed on opposing sides of tissue adjacent the bodily opening when in the expanded state.

33. The device of claim 1 further comprising a catheter or scope device.

34. The device of claim 33 further comprising a centralizing distal tip.

35. The device of claim 33 further comprising an inner diameter of the catheter accommodating the hook and facilitates collapse of the hook.

36. The device of claim 33 further comprising an outer diameter of the catheter comprising registers for a tip of the hook to keep them concentric within the catheter.

37. The device of claim 33 wherein an outer diameter of the catheter is stepped such that a distal end of the catheter is of a larger diameter than a proximal end of the catheter.

38. The device of claim 33 wherein a distal end of the catheter comprises a curve such that deployed hook tips are rotated and biased away from an edge of a banding system.

* * * * *